United States Patent [19]

Mössle et al.

[11] Patent Number: 4,634,376

[45] Date of Patent: Jan. 6, 1987

[54] TARTAR-REMOVING HANDPIECE

[75] Inventors: Walter Mössle, Bad Waldsee; Eugen Eibofner, Biberach, both of Fed. Rep. of Germany

[73] Assignee: Kaltenbach & Voigt GmbH & Co., Biberach an der Riss, Fed. Rep. of Germany

[21] Appl. No.: 723,821

[22] Filed: Apr. 16, 1985

[30] Foreign Application Priority Data

May 9, 1984 [DE] Fed. Rep. of Germany ....... 3417123

[51] Int. Cl.$^4$ .............................................. A61C 3/00
[52] U.S. Cl. ..................................... 433/29; 433/118; 433/124; 433/127
[58] Field of Search ................ 433/29, 124, 118, 119, 433/120, 127, 128, 126, 130, 132, 100, 87

[56] References Cited

U.S. PATENT DOCUMENTS 3,076,904 2/1963 Kleesattel et al. .................. 433/118
4,484,893 11/1984 Finn ...................................... 433/29
4,518,355 5/1985 Hoffmeister et al. ............... 433/128

FOREIGN PATENT DOCUMENTS 3328604 2/1985 Fed. Rep. of Germany ........ 433/29

Primary Examiner—John J. Wilson
Attorney, Agent, or Firm—Scully, Scott, Murphy & Presser

[57] ABSTRACT

A tartar-removing or scaling handpiece, which is constituted of an elongated gripping sleeve, having arranged at one end thereof a tartar-removing or scaling implement which includes a bent operating end, wherein the gripping sleeve incorporates a light source arranged at the end thereof proximate the implement which is oriented towards the region of the tartar-removing implement, and which is located at one side adjacent the tartar-removing implement. The tartar-removing implement possesses a shaft connected with the gripping sleeve, to which there is joined the angled or curvilinearly bent operating end of the implement.

15 Claims, 13 Drawing Figures

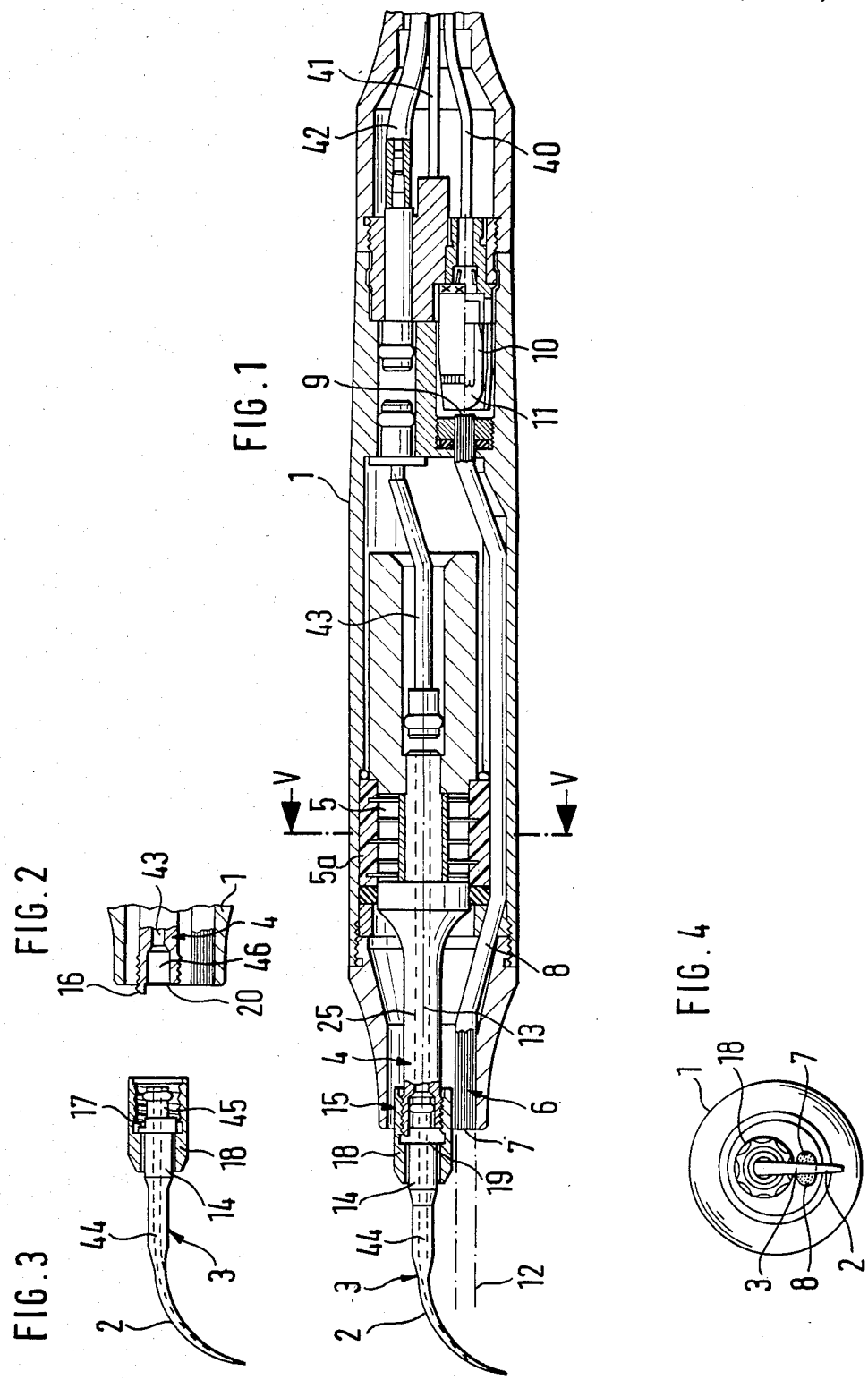

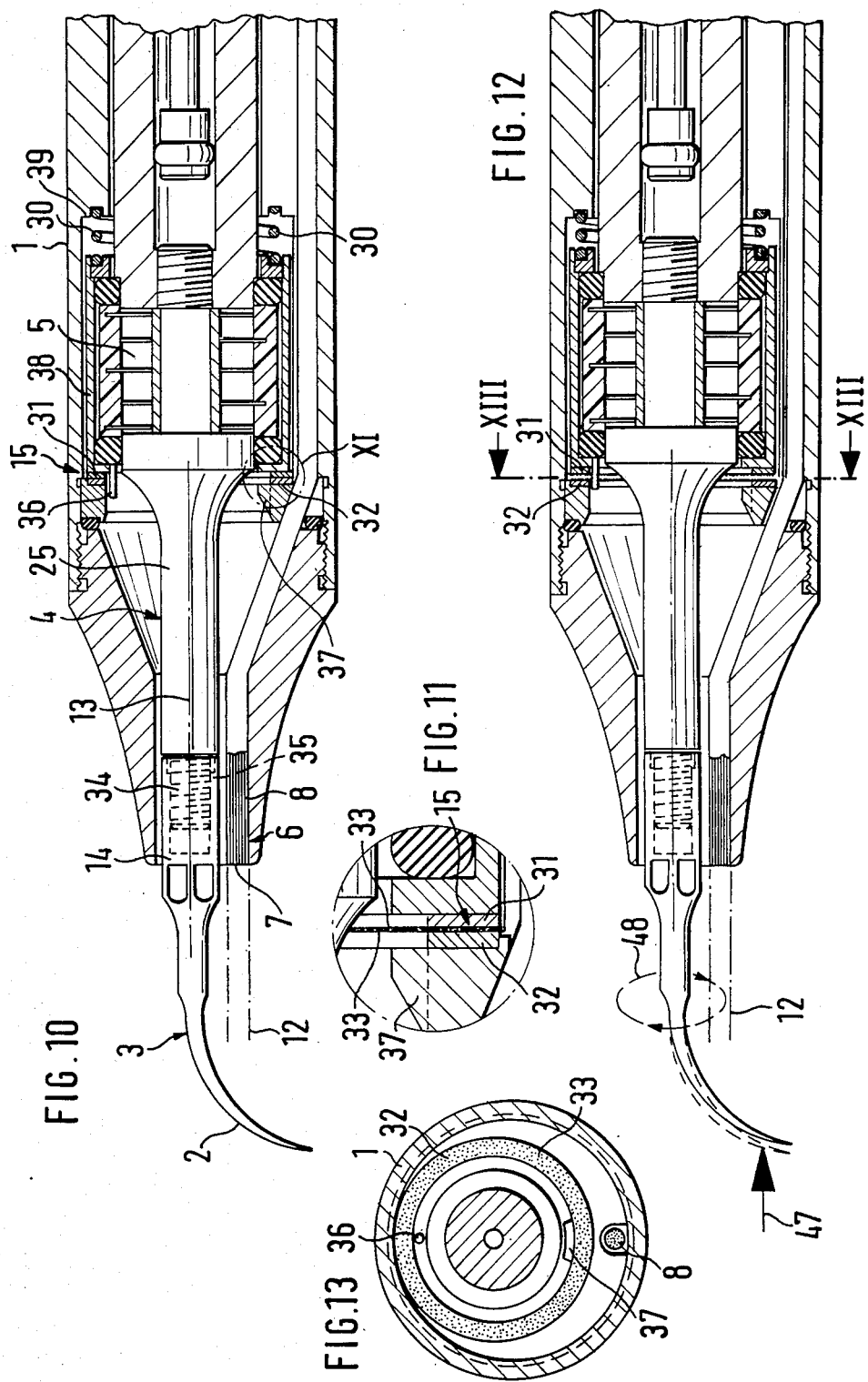

TARTAR-REMOVING HANDPIECE

BACKGROUND OF THE INVENTION

1. Field of the Invention

The present invention relates to a tartar-removing or scaling handpiece, which is constituted of an elongated gripping sleeve, having arranged at one end thereof a tartar-removing or scaling implement which includes a bent operating end, wherein the gripping sleeve incorporates a light source arranged at the end thereof proximate the implement which is oriented towards the region of the tartar-removing implement, and which is located at one side adjacent the tartar-removing implement. The tartar-removing implement possesses a shaft connected with the gripping sleeve, to which there is joined the angled or curvilinearly bent operating end of the implement.

2. Discussion of the Prior Art

A tartar-removing or scaling handpiece of the above-mentioned type belongs to the currently known state of the art, as is illustrated in FIG. 13 of U.S. Pat. Application No. 634,784, now U.S. Pat. No. 4,578,033, issued 03/25/76. In this handpiece, which is representative of the state of the art, the light source, which is shaped as a light conductor, is arranged besides the shaft of the tartar-removing implement.

When the implement is detachably inserted into the gripping sleeve, it is possible that the light source and the bent operating end of the implement, subsequent to the insertion of the implement into the gripping sleeve, can find themselves in such a mutually offset position that the light beam of the light source will pass by the bent operating end of the implement, and as a result, the region of the operating end of the implement will be either inadequately illuminated or even unilluminated.

SUMMARY OF THE INVENTION

Accordingly, the present invention, as described in detail hereinbelow, has as its object to provide a tartar-removing or scraping implement of the above-mentioned type, which will ensure that subsequent to the insertion of the tartar-removing implement into the gripping sleeve there is assured in a simple manner a rotational positioning of the implement affording an optimized illumination of the region of the operating end of the implement.

The advantages which are achieved through the present invention can be essentially ascertained in that merely engaging or latching means must be brought into cooperating engagement during the insertion or subsequent to the insertion of the implement, such that the light beam will impinge the bent operating end of the implement, and there is consequently afforded a satisfactory illumination of the operating end.

Advantageous additional modifications and features of the invention may be ascertained from the following detailed description of exemplary embodiments thereof.

BRIEF DESCRIPTION OF THE DRAWINGS

Reference may now be had to the following detailed description of exemplary embodiments of the invention, taken in conjunction with the accompanying drawings; in which:

FIG. 1 illustrates a longitudinal section through a tartar-removing handpiece with an inserted tartar-removing or scaling implement;

FIG. 2 illustrates a fragmentary longitudinal sectional view through the end of the tartar-removing handpiece towards the implement with the implement having been removed;

FIG. 3 illustrates a sectional view of the removed implement with its coupling nut;

FIG. 4 illustrates an end view of the handpiece of FIG. 1 facing towards the implement;

FIG. 10 illustrates the implement end of a further modified embodiment of the tartar-removing handpiece, shown in a longitudinal section;

FIG. 11 illustrates, on an enlarged scale, the detail shown in the encircled portion XI in FIG. 10;

FIG. 12 illustrates the handpiece of FIG. 10 with the implement shown inserted into the gripping sleeve; and FIG. 13 illustrates a sectional view taken along line XIII—XIII in FIG. 12.

DETAILED DESCRIPTION

Figure 6:
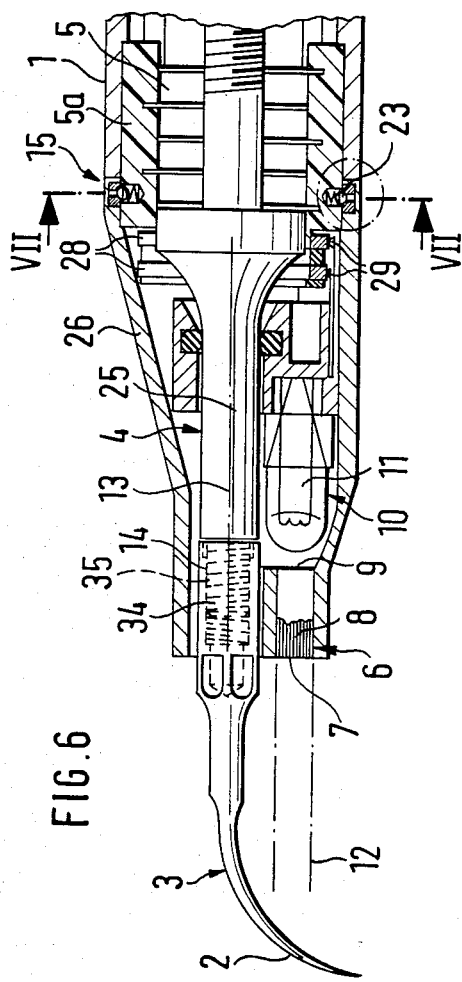
FIG. 6 illustrates a longitudinal sectional view of a modified embodiment of a tartar-removing handpiece at the implement end thereof.
Figure 7:
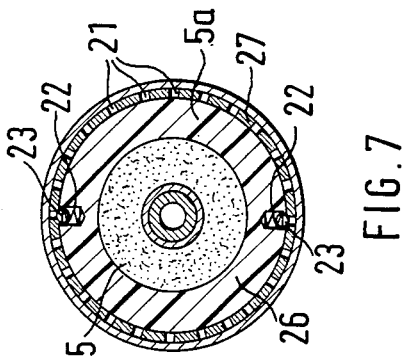
FIG. 7 illustrates a sectional view taken along line VII—VII in FIG. 6.

The tartar-removing or scaling handpiece consists of an elongated gripping sleeve 1 at one end of which there is arranged a tartar-removing or scaling implement 3 which includes a bent operating end 2. For example, the implement 3 can be constructed as a simple scraper or a scaler, and can be directly connected with the gripping sleeve 1; for instance, screwed or clamped. However, the implement 3 can also be vibratable and, as illustrated, for transmission of vibrations can be connected with the implement carrier 4 of a vibration generator 5 which is located within the gripping sleeve 1. The vibration generator 5 can be pneumatically actuatable, or electrically actuatable as shown in the illustrated case.

The gripping sleeve 1 at its end facing the implement, possesses a light source 6 which is directed towards the region of the tartar-removing implement 3, and which is arranged at one side adjacent the implement 3. The light source 6 can be arranged externally on the gripping sleeve 1, or as illustrated, within the gripping sleeve 1; in effect, extending from the end thereof facing the implement. The light source 6, for instance, can further be constituted of an electric light bulb or, as illustrated, of a fiber-shaped end 7 of a light conductor 8 facing the implement, whose end 9 which is distant from the implement is supplied with light, for example, through the end of a further light conductor or as illustrated, by a light bulb 11.

The tartar-removing or scaling implement 3 is detachably inserted into the gripping sleeve 1; in essence, detachably connected with the implement carrier 4 of the vibration generator 5. For the fixing the rotational position of the implement 3 assumable through turning about the axis 13 of the implement shaft 14, which will effect the alignment of a light beam 12 emanating from the light source 6 with the bent operating end 2 of the tartar-removing implement 3, there are provided mutually cooperating latching means 15.

The latching means 15 are formed by, respectively, at least one engaging means on the shaft 14 of the implement 3 and one on the handpiece, in effect on the implement carrier 4, whereby the engaging means are interengagable or latchable with each other in the rotational position of the implement 3 effecting the alignment of the light beam 12 and the bent operating end 2.

In the embodiment pursuant to FIGS. 1 through 5, the one engaging means is formed by a gib or protuberance 16 which extending axially from implement carrier 4 of the handpiece at the end towards the implement, while the other engaging means is formed by a recess 17 in the shape of a flat in the implement shaft 14 which receives the protuberance 16. The implement 3 and the handpiece, in effect, the implement carrier 4, are latchable with each other by means of a coupling nut 18 by being drawn together in a rotational position which will effect the alignment of the light beam 12 and the bent operative end 2 as well as the mutual interengagement of the engaging means. Prior thereto, the implement 3 is inserted with an extension 45 of its shaft 14 into a blind bore 46 provided in the end surface of the implement carrier or support 4. The coupling nut 18 also possesses an internal collar 19 for the axial contact with a collar 20 on the implement carrier 4.

Figure 5:
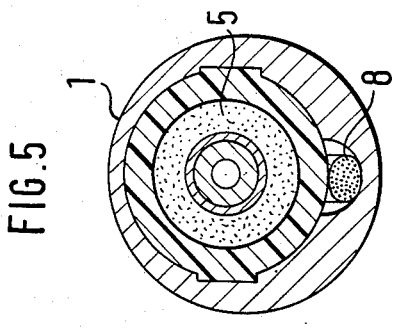
FIG. 5 illustrates a sectional view taken along line V—V in FIG. 1.

From FIG. 5 there can be ascertained the arrangement for securing the vibration generator 5 against rotation within the gripping sleeve 1. When the protuberance 16 and the recess 17 are brought into engagement with each other, there is then assured the impingement of the light beam 12 against the operating end 2 of the implement 3.

Figure 8:
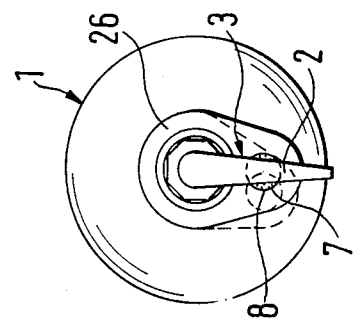
FIG. 8 illustrates an end view of the handpiece of FIG. 6 facing towards the implement.
Figure 9:
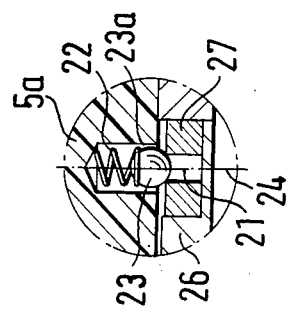
FIG. 9 illustrates, on an enlarged scale, the detail shown in the encircled portion IX in FIG. 6.

In the exemplary embodiment pursuant to FIGS. 6 through 9, the one engaging means is formed by latching recesses 21 which are distributed about a circle which has its center point located in the axis 13 of the implement shaft 14, while the other engaging means is constituted of at least one latching member 23 which, under the biasing action of a spring 22, will engage in one of the latching recesses 21 according to the rotational position of the implement 3. The spring 22 is presently formed as a helical compression spring. As can be ascertained, there are provided a total of two diametrically oppositely located latching members which are formed as latching balls. The latching members 23 can then be basically axially engagable into the suitably located latching recesses 21. In the illustrated instance, the latching members are, however, also engagable in a radial direction into the latching recess 21 which presently possesses one radially extending axis 24, as shown in FIG. 9.

The spring 22 and the latching member 23 are respectively located in a blind bore 23a in an isolator 5a for the vibration generator 5. The latching recesses 21 are arranged in a locking ring 27 secured against rotation with the inner wall of the handpiece.

In detail, the latching members 23 are arranged on an extension 25 which is secured against rotation to the implement 3, and the latching recesses 21 are located on the inner wall of a separate rotatable cap 26 which forms the part of the gripping sleeve part at the implement end and which is rotatable relative to the remaining gripping sleeve 1 about the axis 13 of the implement shaft 14.

Interiorly of the cap 24 there is arranged the light bulb 11 as the light-supplying element 10 for a short light conductor 8. The light conductor 8 and the light bulb 11 are rotatable in conjunction with the cap 26. For this purpose, there are provided stationary contact rings 28, as well as slide contacts 29 which are rotatable together with the cap 26 and which contact the contact rings 28 for the supply of current to the light bulb 11. The vibration generator 5 is secured against rotation together with the implement carrier 4 and the implement 3, and contains the latching members 23. The collet or locking ring 27 is arranged at the end of the cap 26, which faces away from the implement. In FIG. 8 there is illustrated, by means of phantom lines, one position of the cap 26 rotated in the clockwise direction.

Insofar as the previously loosened implement 3 after its connection with the implement carrier 4, or with the extension 25, assumes a rotational position in which the light beam 12 passes by the bent operating end 2, then the cap 26 need only be turned about the axis 13 until the latching members 23 lock in a position in which the light beam 12 and the operating end 2 are in alignment with each other.

In the embodiment according to FIGS. 10 through 13, the implement 3 which is inserted into the gripping sleeve 1 is axially movable from a pressure-applying position opposite the action of a return spring 30, in which the implement 3 has one pressure surface 31 contacting against a complementary pressure surface 32 on the gripping sleeve 1, into a non-pressuring position which allows for the rotation of the implement 3 about the axis 13 of the implement shaft 14, whereby the one engaging means is formed by the pressure surface 31 and the other engaging means by the complementary pressure surface 32. The pressure surface 31, as well as the complementary pressure surface 32 are each provided with a friction facing 33 so as to improve the degree of adhesion, or in effect, the extent of interengagement.

Furthermore, the pressure surface 31, as well as the complementary pressure surface 32 are each located in a radial plane. The pressure surface 31 is arranged on an extension 25 which is secured against rotation together with the implement 3, which is also in this instance formed by the implement carrier 4 which is connected with the vibration generator 5 located within the gripping sleeve 1.

The implement 3 is screwed together with the extension 25. For this purpose, the end of the extension 25 facing the implement possesses a protuberance 34 which is provided with an external screw thread, and the end of the implement shaft 14 facing the gripping sleeve incorporates a blind bore 35 which is provided with an internal screw thread. The implement 3, in a manner not shown herein, can also be connected, through the intermediary of a collet or the like, with the implement carrier 4. The implement 3 and the gripping sleeve 1 are additionally provided with a turn limiting guard which is formed by a stop 36 associated with one of the pressure surfaces 31 of the implement 3, and a cooperating stop 37 associated with the complementary pressure surface 32 on the gripping sleeve 1. The stop 36 is constructed in the shape of a pin, and the complementary stop 37 in a form of a cam.

In order to assume the non-pressing position, the implement 3 together with its shaft 14 is slidable into the gripping sleeve 1. Hereby, there is concurrently slid along therewith the vibration generator 5 which is supported within a sliding sleeve 38. The return spring 30 which is supported against an internal annular projection 39 in the gripping sleeve 1, and which is formed as a helical compression spring, consequently presses against the end of the sliding sleeve 38 which is distant from the implement.

In the event that the previously released implement 3 has assumed a rotational position after its connection with the implement carrier 4 or with the extension 25, in which the light beam 12 passes by the bent operating end 2, then the implement 3 with its shaft 14, and thereby with the extension 25 as well as with the vibration generator 5, need merely be pressed opposite the direction of the spring 30, in the direction of the arrow 47 in FIG. 12, into the gripping sleeve 1, whereby the pressure surface 31 according to FIG. 12 will loosen from the complementary pressure surface 32; whereupon the implement can be turned for so long about the axis 13 as illustrated by the round arrow 48, until the light beam 12 and the operating end 2 will be in alignment. At that time, the pressure on the implement 3 can be ended, in view of which responsive to the action of the return spring 30, the pressure surface 31 will again come into contact with the complementary pressure surface 32, and as a result the implement 30 can no longer be turned any further.

In FIG. 1, the reference numeral 40 designates the electrical power supply conduit for the light bulb 11; 41 the electrical power supply conduit for the vibration generator 5; and 42 designates a cooling medium conduit. The cooling medium which flows through the cooling medium conduit 42 passes through a therewith connected cooling medium passageway 43 into a hollow channel 44 in the implement 3, and from there to the treating location.

What is claimed is:

1. In a tartar-removing handpiece, including an elongated gripping sleeve, a tartar-removing implement having a bent operating end being arranged at one end of said gripping sleeve, said gripping sleeve having a light source at the end facing said implement, said light source being directed towards the region of the tartar-removing implement and being located at one side adjacent the tartar-removing implement; the improvement comprising: said tartar-removing implement is inserted into the gripping sleeve; and latching means for fixing the rotational position of the implement for aligning a light beam emanating from the light source with the bent operating end of the tartar-removing implement, said latching means comprising at least one engaging means on the implement and cooperative engaging means on the handpiece, wherein the engaging means and cooperative engaging means are engagable with each other in the rotational position of the implement effecting the alignment of the light beam and the bent operating end, one said engaging means being formed by an axially projecting protuberance and the cooperative engaging means comprising a recess for receiving the protuberance.

2. A handpiece as claimed in claim 1, comprising a coupling nut for locking the implement and the handpiece in the rotational position thereof effecting the alignment of the light beam and the bent operating end and the mutual engagement of said latching means.

3. In a tartar-removing handpiece, including an elongated gripping sleeve; a tartar-removing implement having a bent operating end being arranged at one end of said gripping sleeve, said gripping sleeve having a light source at the end facing said implement, said light source being directed towards the region of the tartar-removing implement and being located at one side adjacent the tartar-removing implement; the improvement comprising: said tartar-removing implement is inserted into the gripping sleeve; and latching means for fixing the rotational position of the implement for aligning a light beam emanating from the light source with the bent operating end of the tartar-removing implement, said latching means comprising at least one engaging means on the implement and cooperative engaging means on the handpiece, wherein the engaging means and cooperative engaging means are engagable with each other in the rotational position of the implement effecting the alignment of the light beam and the bent operating end, one said engaging means comprising latching recesses distributed about a circle having the center point thereof in the axis of a shaft of the implement; and the cooperating engaging means comprising at least one latching member engaging into one of the latching recesses responsive to the rotational positioning of the implement under the biasing action of a spring.

4. A handpiece as claimed in claim 3, wherein said at least one latching member is engagable in a radial direction into the latching recesses, said latching recesses being formed in the inner wall of the handpiece.

5. A handpiece as claimed in claim 4, wherein said at least one latching member is arranged on an extension secured against rotation with the implement, and the latching recesses are formed in the inner wall of a separate cap forming the gripping sleeve portion facing said implement, said cap being rotatable about the axis of the implement shaft relative to the remaining gripping sleeve.

6. A handpiece as claimed in claim 5, wherein the extension of the implement comprises an implement carrier connected with a vibration generator arranged within the gripping sleeve.

7. A handpiece as claimed in claim 6, wherein the implement is threadingly interconnected with the extension.

8. A handpiece as claimed in claim 7, wherein the end of the extension facing said implement includes a projection having an external screw thread, and the end of the implement facing said gripping sleeve includes a blind bore having an internal screw thread adapted to cooperate with said external screw thread.

9. In a tartar-removing handpiece, including an elongaged gripping sleeve; a tartar-removing implement having a bent operating end being arranged at one end of said gripping sleeve, said gripping sleeve having a light source at the end facing said implement, said light source being directed towards the region of the tartar-removing implement and being located at one side adjacent the tartar-removing implement; the improvement comprising: said tartar-removing implement is inserted into the gripping sleeve; and latching means for fixing the rotational position of the implement for aligning a light beam emanating from the light source with the bent operating end of the tartar-removing implement, said latching means comprising at least one engaging means on the implement and cooperative engaging means on the handpiece, wherein the engaging means and cooperative engaging means are engagable with each other in the rotational position of the implement effecting the alignment of the light beam and the bent operating end, said implement being axially movable opposite the biasing force of a return spring from a pressure-applying position in which the implement has a pressure surface contacting against a complementary pressure surface on the gripping sleeve, into a non-pressuring position in which there is facilitated the rotation of the implement about the axis of the implement shaft, one said engaging means being the pressure surface and the cooperating engaging means being the complementary pressure surface.

10. A handpiece as claimed in claim 9, wherein the pressure surface and the complementary pressure surface are provided with friction facings.

11. A handpiece as claimed in claim 9, wherein the pressure surface and the complementary surface extend in radial planes.

12. A handpiece as claimed in claim 9, wherein the pressure surface is arranged on an extension secured against rotation with the implement.

13. A handpiece as claimed in claim 9, wherein the implement and the gripping sleeve are provided with rotation limiting guard means.

14. A handpiece as claimed in claim 13, wherein the rotation limiting guard means comprises a stop associated with the pressure surface on said implement and complementary stop associated with the complementary pressure surface on said gripping sleeve.

15. A handpiece as claimed in claim 9, wherein the implement is movable into the gripping sleeve for assuming the non-pressuring position thereof.

* * * * *